United States Patent [19]

Campbell et al.

[11] 4,289,772
[45] Sep. 15, 1981

[54] 1-PIPERIDINOPHTHALAZINES AS CARDIAC STIMULANTS

[75] Inventors: Simon F. Campbell, Deal; John C. Danilewicz; Anthony G. Evans, both of Ash, Nr. Canterbury; Allan L. Ham, Broadstairs, all of England

[73] Assignee: Pfizer Inc., New York, N.Y.

[21] Appl. No.: 103,342

[22] Filed: Dec. 13, 1979

Related U.S. Application Data

[62] Division of Ser. No. 908,664, May 23, 1978.

[30] Foreign Application Priority Data

Jun. 3, 1977 [GB] United Kingdom ............... 23582/77

[51] Int. Cl.³ .......................................... A61K 31/495
[52] U.S. Cl. ................................................... 424/250
[58] Field of Search ........................................ 424/250

[56] References Cited

U.S. PATENT DOCUMENTS 3,478,028 11/1969 Parsons et al. ...................... 544/237
3,753,988 8/1973 Rodway et al. ..................... 544/237

FOREIGN PATENT DOCUMENTS 1199768 7/1970 United Kingdom .
1293565 10/1972 United Kingdom .
1460389 1/1977 United Kingdom .

Primary Examiner—Anna P. Fagelson
Attorney, Agent, or Firm—Connolly and Hutz

[57] ABSTRACT

A series of 1-piperidinophthalazine derivatives as phosphodiesterase inhibitors and cardiac stimulants.

20 Claims, No Drawings

1-PIPERIDINOPHTHALAZINES AS CARDIAC STIMULANTS

This application is a division of application Ser. No. 908,664, filed May 23, 1978.

BACKGROUND OF THE INVENTION

1. Field of the Invention

This invention relates to novel cardiac stimulants and, in particular, to 1-(1-piperidino)phthalazines and the pharmaceutically acceptable acid addition salts thereof.

2. Description of the Prior Art

Quinazolines, reported to be cardiac stimulants, are claimed in U.S. Pat. No. 4,001,422.

British Pat. No. 1,293,565 claims a series of 1-amino-4-arl- and aralkylphthalazine derivatives as anti-inflammatory and anti-rheumatic agents. None of the compounds are reported to be cardiac stimulants.

British Pat. No. 1,133,406 describes a group of 1,4-diaminophthalazines which are useful as antipyretic, anti-inflammatory, hypotensive, bronchodilator and respiratory stimulant agents.

British Pat. No. 1,199,768 discloses a limited number of 4-aminoquinazoline derivatives as antihypertensive agents.

SUMMARY OF THE INVENTION

The phthalazine compounds of this invention are of the formula:

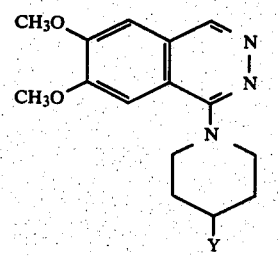

and a pharmaceutically acceptable acid addition salt thereof, wherein Y is selected from the group consisting of —$CH_2COR_1$ wherein $R_1$ is alkyl having one to four carbon atoms or alkoxy having one to four carbon atoms;

—$N(R_2)COR_3$ wherein $R_2$ is hydrogen or alkyl having one to four carbon atoms and $R_3$ is alkyl having one to four carbon atoms, alkoxy having one to four carbon atoms, phenyl or benzyloxy;

—$N(R_2)SO_2R_4$ wherein $R_2$ is hydrogen or alkyl having one to four carbon atoms and $R_4$ is alkyl having one to four carbon atoms, phenyl, pyridyl, benzyl or dialkoxyphenyl wherein said alkoxy contains one to four carbon atoms;

—$N(R_2)CONR_5R_6$ wherein $R_2$ is hydrogen or alkyl having one to four carbon atoms, $R_5$ is alkyl having one to four carbon atoms, benzyl or pyridyl and $R_6$ is hydrogen or alkyl having one to four carbon atoms;

—O—$CONHR_7$ wherein $R_7$ is alkyl having one to four carbon atoms, phenyl, benzyl or pyridyl;

hydroxy;

alkanoyloxy having one to four carbon atoms;

alkoxy of one to four carbon atoms;

substituted alkyl wherein said alkyl contains one to five carbon atoms and said substituent is hydroxy, alkoxy having from 1 to 4 carbon atoms or —$CONR_2R_6$ wherein $R_2$ and $R_6$ are each hydrogen or alkyl having one to four carbon atoms; and substituted alkoxy wherein said alkoxy contains two to four carbon atoms and said substituent is hydroxy or alkoxy having one to four carbon atoms, with the proviso that other than the alpha-carbon atom is substituted.

Especially preferred along with their pharmaceutically acceptable acid addition salts are those compounds wherein Y is —$CH_2COR_1$ wherein $R_1$ is alkyl having one to four carbon atoms;

—$N(R_2)SO_1R_3$ wherein $R_2$ is methyl;

—$N(R_2)CONR_5R_6$ wherein $R_2$ is methyl and $R_5$ and $R_6$ are each alkyl having one to four carbon atoms;

—O—$CONHR_7$ wherein $R_7$ is alkyl having one to four carbon atoms;

—substituted alkyl; and

—substituted alkoxy.

Those compounds and their pharmaceutically acceptable acid addition salts which are preferred are of the formula:

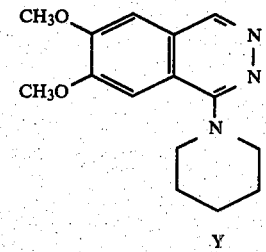

wherein Y is selected from the group consisting of
—$OCONHC_2H_5$
—$OCH_2C(CH_3)_2OH$
—$CH_2CH_2OCH(CH_3)_2$
—$N(CH_3)CON(CH_3)_2$
—$N(CH_3)SO_2CH_3$
—$N(CH_3)SO_2.(CH_2)_2CH_3$
—$N(CH_3)SO_2.benzyl$
—$N(CH_3)SO_2.3-pyridyl$
—$N(CH_3)SO_2.phenyl$
—$N(CH_3)CO(CH_2)_2CH_3$
—$CH_2COCH_3$
and
—$CH_2CH_2CON(CH_3)_2$.

The compounds of this invention containing one or more asymmetric centers will exist as one or more pairs of enantiomers, and such pairs or individual isomers may be separable by physical methods, e.g. by fraction crystallization of the free bases or suitable salts or chromatography of the free bases. The invention includes the separated pairs as well as mixtures thereof, as racemic mixtures or as separated D- and L- optically-active isomeric forms.

The pharmaceutically acceptable acid addition salts of the compounds of the invention are those formed from acids which form non-toxic acid addition salts containing pharmaceutically acceptable anions, such as the hydrochloride, hydrobromide, hydroiodide, sulphate or bisulfate, phosphate or acid phosphate, acetate, maleate, fumarate, lactate, tartrate, citrate, gluconate, saccharate and p-toluene-sulphonate salts.

Also included within the scope of the present invention are "pharmaceutically acceptable bioprecursors" of the claimed compounds.

The term "pharmaceutically acceptable bioprecursor" used above requires some explanation. It is, of course, common practice in pharmaceutical chemistry to overcome some undesirable physical or chemical property of a drug by converting the drug into a chemical derivative which does not suffer from that undesirable property, but which, upon administration to an animal or human being, is converted back to the parent drug. Again, if the drug is unstable in solution, it may be possible to prepare a chemical derivative of the drug which is stable and may be administered in solution, but which is reconverted in the body to give the parent drug. The pharmaceutical chemist is well aware of the possibility of overcoming intrinsic deficiencies in a drug by chemical modifications which are only temporary and are reversible upon administration to the animal or patient.

For the purpose of this invention the term "pharmaceutically acceptable bioprecursor" of a compound of the formula (I) means a compound having a structural formula different from the compounds of the formula (I) but which nonetheless, upon administration to an animal or human being, is converted in the patient's body to a compound of the formula (I).

DETAILED DESCRIPTION OF THE INVENTION

The compounds of the present invention can be synthesized by a number of routes:

Route A

Compounds of the formula (I) may be prepared by reacting an appropriately substituted phthalazine of the formula:

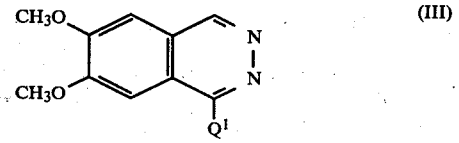

(III)

wherein $Q^1$ represents a leaving group such as chloro-, bromo-, iodo-, lower alkoxy or (lower alkyl)thio, with an amine of the formula:

(IV)

with resultant elimination of $HQ^1$. $Q^1$ is preferably chloro or bromo. The reaction is preferably carried out in an inert organic solvent such as isoamyl alcohol with heating, e.g. under reflux, in a temperature range of 75° to 150° C. for up to 24 hours. When $Q^1$ is chloro-, bromo- or iodo-, the presence of a base such as triethylamine or of excess reagent of the formula (IV) is advantageous.

Any substituent groups in the reactants capable of displacing the leaving group $Q^1$, other than the:

group of the compound of the formula (IV), i.e. hydroxy, primary amino and secondary amino groups, should generally be protected prior to the reaction by conventional methods, the protecting groups being removed after the reaction by standard procedures. Any hydroxy groups present may, if necessary, be protected by, for example, a benzyl group, which group may be removed after the reaction by hydrogenolysis. Any primary or secondary amino groups may, if necessary, be protected by, e.g. a benzyl or t-butoxycarbonyl group, which groups can be removed after the reaction by, respectively, hydrogenation or mild acid hydrolysis.

The product may be isolated and purified by conventional methods.

Route B

Compounds of the formula (I) in which Y is $-N(R_2)CONHR_5$ may be prepared by reacting a phthalazine of the formula:

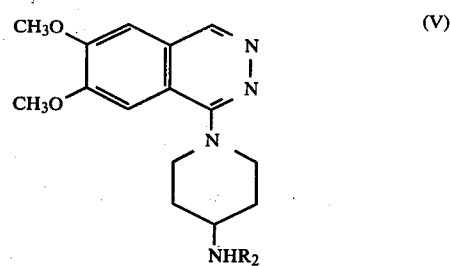

(V)

with an isocyanate $R_5NCO$, $R_5$ being other than hydrogen, or, to prepare compounds wherein $R_5$ is H, sodium or potassium cyanate in the presence of acid. The acid may be supplied by using an acid addition salt of the compound of the formula (V) as the starting material.

In a typical procedure, the phthalazine and isocyanate are heated together, e.g. under reflux, in a suitable organic solvent, e.g. chloroform, for from 12 to 24 hours. The product may be isolated and purified by conventional procedures.

Any groups capable of reacting with isocyanate groups or, as appropriate with the cyanate, other than of course the $-NH-$ group of $-NHR_2$ in the piperidino ring, should generally be protected by conventional protecting groups prior to the reaction, the protecting group being removed by standard procedures after the reaction. Groups which it may be necessary to protect include hydroxy, primary amino and secondary amino groups.

Route C

Compounds of the formula (I) wherein Y is either $-N(R_2)COR_3$, $-N(R_3)SO_2R_4$ or $-N(R_2)CONR_5R_6$, may be prepared by reacting a compound of the formula (V) as previously defined with, as appropriate, either: (a) a haloformate or acyl halide of the formula $Q^2COR_3$ wherein $Q^2$ is chloro or bromo; (b) a halosulfonate, sulfonyl halide or sulfamyl halide of the formula $Q^2SO_2R_4$, $Q^2$ being chloro or bromo; (c) a carbamyl halide of the formula $R_5R_6NCOQ^2$ wherein $R_5$ and $R_6$ are both other than hydrogen, and $Q^2$ is chloro or bromo; or (d) an anhydride or pyrocarbonate of the formula $(R_3CO)_2O$.

Typically the reactants are allowed to stand together at room temperature for a period of up to about 72 hours in an inert organic solvent, e.g. chloroform, in the presence of a base such as triethylamine.

Any groups in $R_2$ to $R_7$ capable of reacting with, or displacing as appropriate, the anhydride, pyrocarbonate or the group $Q^2$, e.g. hydroxy, primary amino, and secondary amino groups, should, if necessary, be protected prior to the reaction by conventional protecting groups which may be removed after the reaction by standard procedures.

The product may be isolated and purified by conventional methods.

Route D

Compounds of the formula (I) wherein Y is —O—CONHR$_7$ may be prepared by reacting a phthalazine of the formula:

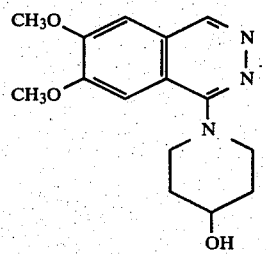

(VI)

with an isocyanate $R_7NCO$, $R_7$ being other than hydrogen, or, to prepare compounds in which $R_7$ is hydrogen, sodium or potassium cyanate in the presence of acid.

In a typical procedure, the phthalazine and isocyanate are heated together, e.g. under reflux, in a suitable organic solvent, e.g. chloroform, in the presence of a base such as triethylamine for up to about 12 hours.

Any groups capable of reacting with isocyanate groups, or, as appropriate, with the cyanate, other than of course, the —OH group of the piperidino ring, should, if necessary, be protected prior to reaction e.g. in the same manner as that described under Route B. The final product may be isolated by conventional methods.

Route E

Compounds of the formula (I) wherein Y is —NHCONR$_5$R$_6$ may be prepared by initially reacting a phthalazine of the formula:

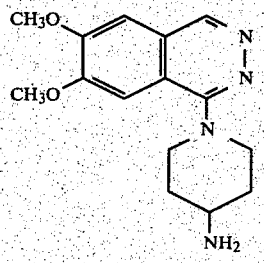

(VII)

with phosgene, typically in the presence of a base, e.g. triethylamine and in the presence of an inert solvent such as chloroform or toluene, the —NH$_2$ group being converted to an —NCO group. A compound of the formula $R_5R_6NH$ is then added to the reaction mixture to react with the —NCO group. If desired, the intermediate —NCO containing phthalazine may be isolated and optionally purified before reaction with the compound $R_5R_6NH$.

Any hydroxy groups, primary amino groups (other than, of course, the —NH$_2$ group attached to the piperidine ring), and secondary amino groups, should, if necessary, be protected by conventional protecting groups prior to the reaction, the groups being removed by standard procedures after the reaction.

The product may be isolated and purified by conventional procedures.

Route F

Compounds of the formula (I) in which Y is —N(R$_2$)COR$_3$, R$_3$ being other than lower alkoxy, substituted lower alkoxy and aryloxy, may be prepared by reacting a phthalazine of the formula (V) as previously defined with an ester of N-hydroxy succinimide of the formula:

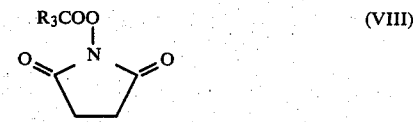

(VIII)

in which R$_3$ is other than lower alkoxy, substituted alkoxy and aryloxy.

Any hydroxy groups or primary or secondary amino groups should, if necessary, be protected prior to the reaction by conventional protecting groups which may be removed after the reaction by standard procedures.

The product may be isolated by conventional methods.

Route G

Compounds of the formula (I) wherein Y is a lower alkyl group substituted by a group of the formula —CONR$_2$R$_6$ can be prepared by reacting a compound of the formula:

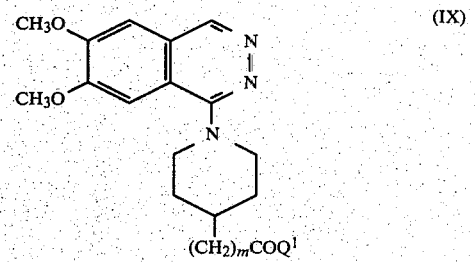

(IX)

wherein $Q^1$ is a good leaving group, and m is 1 to 5, with a compound $R_2R_6NH$. Typical good leaving groups are chloro,

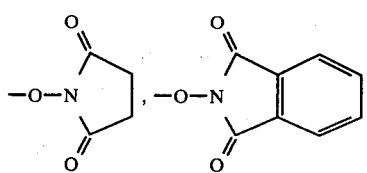

bromo, lower alkoxy, and groups of the formula

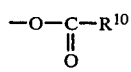

wherein $R^{10}$ is a lower alkyl or lower alkoxy group.

The starting materials of the formula (IX) may be prepared by conventional procedures. For example, the acid chlorides and bromides may be prepared by reacting the corresponding free acid with thionyl chloride or bromide. Similarly the succinimido and phthalimido esters may be prepared by reacting the free acid with N-hydroxy-succinimide or -phthalamide. Again the mixed anhydrides of the formula (IX) may be prepared by reacting the corresponding free acid with a lower alkanoyl chloride or bromide, or a lower alkyl chloroformate or bromoformate.

Any substituent groups in $R_2$ and $R_6$ capable of reacting with the group $—(CH_2)_m COQ^1$, e.g. primary or secondary amino groups, should, if necessary, be protected prior to reaction and the protecting group removed after reaction.

The product may be isolated and purified by conventional methods.

Route H

Compounds of the formula (I) in which Y is $—N(R_2)COR_3$, $R_3$ being a lower alkyl group substituted by an amino group (as hereinbefore defined), may be prepared by reacting a phthalazine of the formula:

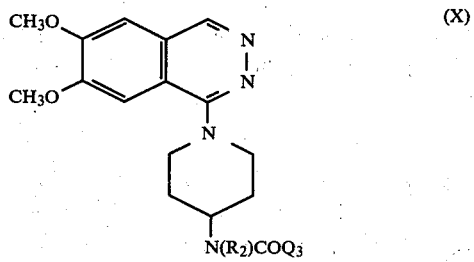

$Q^3$ being lower alkyl substituted by chloro- or bromo-, with a compound of the formula $R_8R_9NH$. Generally, the reaction is carried out in the presence of a base such as triethylamine or excess compound $R_8R_9NH$.

Any substituent groups capable of displacing the group $Q^3$, e.g. hydroxy and primary and secondary amino groups, should, if necessary, be protected prior to the reaction and the protecting group removed after reaction.

The product may be isolated and purified by conventional methods.

Route I

Compounds of the formula (I) in which Y is a lower alkanoyloxy group may be prepared by acylating the corresponding compound in which Y is a hydroxy group with an anhydride of a lower alkanoic acid or a lower alkanoyl chloride or bromide. The reaction may be carried out in a conventional manner. For example, the hydroxy-containing starting material may be heated with the appropriate anhydride (e.g. acetic anhydride) in the presence of the corresponding free acid (e.g. acetic acid) at from 50°–100° C. for up to 24 hours. The product may be isolated and purified by conventional methods.

Any hydroxy group should be protected prior to reaction, the protecting groups being removed afterwards, as described previously.

Route J

In some further cases conversion of one substituent represented by Y to another substituent represented by Y is possible. For example, compounds in which Y is $—CH_2CO$ (lower alkyl) may be prepared by the oxidation ($CrO_3$) of the corresponding compounds in which Y is

(lower alkyl). These latter compounds may in turn be prepared by the alkaline hydrolysis (NaOH) of the corresponding compounds in which Y is

(lower alkyl).

Acid addition salts of the compounds of formula (I) may be prepared from the crude of pure free base product by the conventional technique of reacting the free base with the acid in an inert solvent, e.g. by mixing alcoholic solutions of each and collecting the resulting precipitate by filtration. The product may then be recrystallized to purity.

The phthalazine starting materials used in the preceding routes may be prepared by procedures analogous to those of the prior art. Similarly the piperidine starting materials used in Route A are either known compounds or may be prepared by conventional methods.

The compounds of the invention are phosphodiesterase inhibitors and cardiac stimulants which increase the force of myocardial contract without producing significant increases in heart rate. The compounds are useful in the curative or prophylactic treatment of cardiac conditions, such as congestive heart failure, angina pectoris, cardiac arrhythmias and acute heart failure.

The cardiac stimulant activity of the compounds of the invention is shown by their effectiveness in one or more of the following tests: (a) increasing the force of contraction in the isolated, spontaneously beating, guinea pig double atria preparation; (b) increasing myocardial contractility (left ventricular $dP/d_t$ max.) in the anesthetized dog with an implanted left ventricular catheter; (c) increasing myocardial contractility in the conscious dog with an implanted left ventricular transducer.

In test (a) the positive inotropic and chronotropic response of the atria to the test compound are measured at several doses and compared with the responses elicited by isoprenaline. The comparison of the dose response curves obtained gives a measure of the force versus rate selectively of the test compound.

In test (b) the positive inotropic action of the test compound following intravenous administration is measured in the anesthetized dog. The potency of the inotropic agent, the selectivity for increasing force versus frequency of contraction, and the duration of action of the positive inotropic effect of the test compound are obtained, as are its peripheral effects, e.g. the effect on the blood pressure.

In test (c) the positive inotropic action of the test compound following intravenous or oral administration to a conscious dog with an implanted left ventricular transducer is measured. The potency of the inotropic agent, the selectivity for increasing force versus frequency of contraction, and the duration of action of the inorganic effect of the test compound are all obtained, as are its peripheral effects, e.g. its effect on blood pressure.

The compounds of the invention can be administered alone but will generally be administered in admixture with a pharmaceutical carrier selected with regard to the intended route of administration and standard pharmaceutical practice. They are to be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, it is expected that intravenous dosage of the most active compounds of the invention will be in the range from 1 mg to 300 mg daily, taken in 2 to 4 divided doses per day, for an average adult patient (70 kg). Dosages for intravenous administration would be expected to be within the range 1 to 300 mg per single dose as required, for example in the treatment of acute heart failure. Thus for a typical adult patient individual tablets or capsules might contain from 5 to 500 mg of active compound, in a suitable pharmaceutically acceptable vehicle or carrier.

Thus the present invention provides a pharmaceutical composition comprising a compound of the formula (I) as defined above, or a pharmaceutically acceptable acid addition salt thereof, or a pharmaceutically acceptable bioprecursor therefor, together with a pharmaceutically acceptable diluent or carrier.

The following examples are provided solely for the purpose of illustration and are not to be construed as limitations of this invention, many variations of which are possible without departing from the spirit or scope thereof.

EXAMPLE 1

Preparation of 6,7-Dimethoxy-1-[4-(N-ethylcarbamoyloxy)-piperidino]phthalazine

1-Chloro-6,7-dimethoxyphthalazine (2.69 g) and 4-(ethylcarbamoyloxy)piperidine (4.3 g) were heated together in isoamyl-alcohol (60 ml) at 90° for 18 hours. The mixture was filtered while hot and the filtrate evaporated to dryness in vacuo to give a brown oil which, on trituration with ethyl acetate (30 ml), yielded a solid, which was filtered off. The solid was dissolved in the minimum volume of boiling acetonitrile, while on cooling deposited crystals of unchanged 4-(ethylcarbamoyloxy)piperidine (1.8 g). After filtration, the filtrate was combined with the ethyl acetate trituration liquors and evaporated to dryness in vacuo. The crude product so obtained was suspended in water (50 ml), basified with 5 N sodium hydroxide solution to pH 10, and extracted with chloroform (2×50 ml). After drying the combined chloroform extracts over anhydrous sodium carbonate, the chloroform was evaporated to dryness in vacuo to give a brown oil which was purified by fractionation on a column of powdered silica (bed six 30×25 cm) using chloroform and 2½% methanol in chloroform as eluting solvent. Eighteen 40 ml fractions were collected of which appropriate fractions (identified by t.l.c.) were combined and taken to dryness to give a glassy solid.

This solid was dissolved in warm ethyl acetate (25 ml), cooled, diluted with excess ether and the precipitate was collected. Recrystallization from acetonitrile gave 6,7-dimethoxy-1-[4-(N-ethylcarbamoyloxy)-piperidino]phthalazine (1.6 g) as pale yellow crystals, m.p. 182°–186°.

Analysis %: Found: C, 59.6; H, 6.8; N, 15.8; Calculated for $C_{18}H_{24}N_4O_4$: C, 60.0; H, 6.7; N, 15.6.

(This procedure was repeated using triethylamine in place of excess of said piperidine with the same results).

EXAMPLES 2 TO 33

The following phthalazines were prepared similarly to Example 1, starting from 1-chloro-6,7-dimethoxyphthalazine and the appropriate 4-substituted piperidine:

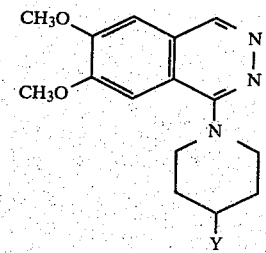

| Example No. | Y | Form Isolated and m.p. (°C.) | Analysis % (Theoretical in brackets) | | |
|---|---|---|---|---|---|
| | | | C | H | N |
| 2 | —OH | Free base, 184–8° | 61.9 (62.3 | 6.9 6.6 | 14.6 14.5) |
| 3 | —NHCONH(CH$_2$)$_3$CH$_3$ | Free base, 192–5° | 61.9 (62.0 | 7.5 7.5 | 18.3 18.1) |

-continued

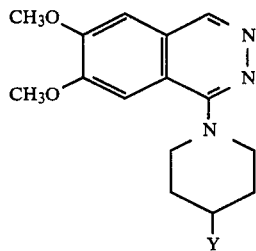

| Example No. | Y | Form Isolated and m.p. (°C.) | Analysis % (Theoretical in brackets) | | |
|---|---|---|---|---|---|
| | | | C | H | N |
| 4 | —NCONH.(CH$_2$)$_2$CH$_3$<br>\|<br>CH$_3$ | Free base,<br>204–7° | 62.2<br>(62.0) | 7.8<br>7.5 | 18.1<br>18.1 |
| 5 | —CH$_2$CH$_2$OH | Free base,<br>168–171° | 64.0<br>(64.3) | 7.4<br>7.3 | 13.7<br>13.2 |
| 6 | —OCH$_3$ | Monohydrate,<br>137° | 60.2<br>(59.8) | 7.3<br>7.2 | 12.9<br>13.1 |
| 7 | —CH$_2$CH$_2$O(CH$_2$)$_3$CH$_3$ | Oxalate,<br>164° | 60.0<br>(59.6) | 6.8<br>7.2 | 9.1<br>9.1 |
| 8 | —CH$_2$COOCH$_2$CH$_3$ | Hydrochloride,<br>200–203° | 57.7<br>(57.7) | 6.6<br>6.6 | 10.9<br>10.6 |
| 9 | —NHCO(CH$_2$)$_2$CH$_3$ | Free base,<br>181–183° | 63.4<br>(63.7) | 7.5<br>7.3 | 15.3<br>15.6 |
| 10 | —OCH$_2$CH(CH$_3$)OCH$_2$CH$_3$ | Oxalate<br>151–152° | 56.5<br>(56.8) | 6.6<br>6.7 | 8.7<br>9.0 |
| 11 | —OCH$_2$CH(OH)CH$_3$ | Free base,<br>132–134° | 62.1<br>(62.2) | 7.2<br>7.3 | 12.2<br>12.1 |
| 12 | —CH$_2$CH$_2$OCH$_3$ | Oxalate,<br>170–173° | 56.8<br>(57.0) | 6.3<br>6.5 | 10.0<br>10.0 |
| 13 | —OCH$_2$C(CH$_3$)$_2$OH | Monohydrate,<br>123–125° | 59.2<br>(60.1) | 7.1<br>7.7 | 11.0<br>11.1 |
| 14 | —NHSO$_2$CH$_3$ | Free base,<br>219–220° | 53.0<br>(52.5) | 6.0<br>6.1 | 16.0<br>15.3 |
| 15 | —CH$_2$CH$_2$OCH(CH$_3$)$_2$ | Hydrochloride<br>dihydrate,<br>190° | 55.4<br>(55.6) | 7.5<br>7.9 | 9.6<br>9.7 |
| 16 | —N(CH$_3$)SO$_2$CH$_3$ | Free base,<br>183–184° | 53.4<br>(53.7) | 6.5<br>6.4 | 14.6<br>14.7 |
| 17 | —N(CH$_3$)SO$_2$(CH$_2$)$_2$CH$_3$ | Free base,<br>204–205° | 55.7<br>(55.9) | 6.7<br>6.9 | 13.7<br>13.7 |
| 18 | —CH$_2$CONH(CH$_2$)$_2$CH$_3$ | Dihydrochloride,<br>125° | 53.8<br>(53.9) | 6.7<br>6.8 | 12.9<br>12.6 |
| 19 | —CH$_2$C(CH$_3$)$_2$OH | Hydrochloride,<br>210° | 59.8<br>(59.8) | 7.5<br>7.4 | 11.0<br>11.0 |
| 20 | —N(CH$_3$)SO$_2$CH$_2$.Phenyl | Monohydrate,<br>133–135° | 58.1<br>(58.2) | 5.9<br>6.4 | 11.9<br>11.8 |
| 21 | —(CH$_2$)$_3$OH | Free base,<br>170–174° | 65.0<br>(65.2) | 7.6<br>7.6 | 13.0<br>12.7 |
| 22 | —(CH$_2$)$_3$CONH$_2$ | Dihydrochloride,<br>200–202° | 53.6<br>(52.9) | 7.4<br>6.5 | 12.7<br>13.0 |
| 23 | —CH$_2$CONHCH$_3$ | Dihydrochloride,<br>200° (decomp.) | 51.3<br>(51.8) | 6.5<br>6.3 | 13.1<br>13.4 |
| 24 | —N(CH$_3$)SO$_2$.(3,4-dimethoxyphenyl) | Hydrochloride,<br>220° (decomp.) | 53.3<br>(53.5) | 5.9<br>5.8 | 9.8<br>10.4 |
| 25 | —OCH$_2$CH$_2$OH | Free base,<br>171–173° | 61.2<br>(61.2) | 6.8<br>7.0 | 12.7<br>12.6 |
| 26 | —N(CH$_3$)SO$_2$.(3-pyridyl) | Hemihydrate,<br>188–189° | 55.8<br>(55.7) | 5.6<br>5.8 | 15.6<br>15.5 |
| 27 | —CH$_2$CH$_2$CONHCH$_3$ | Free base,<br>185–186° | 63.9<br>(63.7) | 7.6<br>7.3 | 16.0<br>15.6 |
| 28 | —N(CH$_3$)SO$_2$.(phenyl) | Free base,<br>187–189° | 59.2<br>(59.7) | 6.0<br>5.9 | 12.5<br>12.7 |
| 29 | —N(CH$_3$)CON(CH$_3$)$_2$ | Hydrochloride,<br>228–230° | 55.5<br>(55.6) | 6.9<br>6.9 | 16.7<br>17.1 |
| 30 | —CH$_2$CH$_2$CON(CH$_3$)$_2$ | Free base,<br>133–134.5° | 64.1<br>(64.5) | 7.5<br>7.6 | 14.8<br>15.0 |
| 31 | —N(CH$_3$)CO.Phenyl | Hydrochloride,<br>1 hydrate,<br>4 247–9° | 61.6<br>(61.7) | 6.2<br>6.2 | 12.5<br>12.5 |
| 32 | —CH$_2$CH$_2$C(CH$_3$)$_2$OH | Free base,<br>148–149° | 66.8<br>(66.8) | 8.2<br>8.1 | 11.5<br>11.7 |
| 33 | —CH$_2$CH$_2$CONH(CH$_2$)$_2$CH$_3$ | Free base,<br>177–179° | 65.1<br>(65.3) | 7.8<br>7.8 | 14.5<br>14.5 |

EXAMPLE 34

Preparation of
6,7-dimethoxy-1-[4-(3'-benzyl-1'-methylureido)-piperidino]phthalazine hydrochloride 6,7-Dimethoxy-1-[4-(N-methylamino)piperidino]phthalazine (prepared from 1.5 g of the oxalate salt) in dry chloroform (30 ml) was treated with benzyl isocyanate (1.5 g) and the resultant mixture was boiled under reflux for 16 hours. The chloroform was then removed by evaporation in vacuo, and the residue re-dissolved in ethyl acetate (5 ml) and applied to a glass column packed with "Florisil" (100 g) (Trade Mark). Elution was accomplished by means of chloroform (1000 ml) and 100 ml fractions were collected. Appropriate fractions were identified by thin-layer chromatography, combined and evaporated. The resulting crude product was dissolved in ethanol (5 ml) and precipitated as the hydrochloride salt by means of hydrogen chloride gas bubbled into the solution. Recrystallization from a mixture of methanol and ether (1:5) gave 6,7-dimethoxy-1-[4-(3'-benzyl-1'-methylureido)-piperidino]phthalazine hydrochloride (0.35 g), m.p. 221°.

N.m.r. (in deuterated trifluoroacetic acid with tetramethylsilane as internal reference standard): chemical shifts (delta, ppm); singlet (3H) 3.15 (NCH$_3$); singlets (3H each) 4.25 and 4.29 (2×OCH$_3$); singlet (2H) 4.66 (benzylic methylene); singlet (5H) 7.35 (protons of benzylic phenyl); singlet (2H) 7.74 (phthalazine protons) and singlet (1H) 9.26 (phthalazine proton).

EXAMPLE 35

Preparation of
6,7-Dimethoxy-1-[4-(N-methylacetamido)-piperidine]phthalazine

Acetic anhydride (0.4 g) was added dropwise to a stirred and cooled solution of 6,7-dimethoxy-1-[4-(N-methylamino)piperidino]phthalazine (1.0 g) and triethylamine (0.8 ml) in dry chloroform (20 ml). The solution was then stirred at room temperature for 18 hours, concentrated in vacuo, the concentrate shaken with water (50 ml), then extracted with chloroform (2×50 ml). The combined organic extracts were shaken with dilute sodium hydroxide (50 ml), then dried over magnesium sulphate and taken to dryness in vacuo, giving a brown oil which was triturated with 30°–40° petroleum ether (70 ml) and the ether decanted. To make the oxalate salt, the residue was dissolved in warm ethyl acetate, filtered, and the filtrate taken to dryness in vacuo and re-dissolved in a small amount of ethyl acetate. The solution was acidified to pH 4 with oxalic acid in ethyl acetate, causing a solid to form which was collected by filtration and crystallized from iso propyl-alcohol to give 6,7-dimethoxy-1-[4-(N-methylacetamido)-piperidino]phthalazine mono-oxalate quarter hydrate (1.0 g), m.p. 211°–214°.

Analysis %: Found: C, 54.8; H, 6.1; N, 12.9 Calculated for $C_{18}H_{24}N_4O_3:C_2H_2O_4.\frac{1}{4}H_2O$: C, 54.7; H, 6.1, N, 12.8.

EXAMPLE 36

6,7-Dimethoxy-1-[4-(N-methyl-n-butyramido)-piperidino]phthalazine hydrochloride hemihydrate was prepared similarly to the previous Example, using n-butyric anhydride in place of acetic anhydride. It had a melting point of 110°–111°.

Analysis %: Found: C, 57.3; H, 7.0; N, 13.7 Calculated for $C_{20}H_{28}N_4O_3.HCl.\frac{1}{2}H_2O$: C, 57.5; H, 7.2; N, 13.4.

EXAMPLE 37

Preparation of
6,7-Dimethoxy-1-[4-(N-ethoxycarbonyl-N-methylamino)piperidino]phthalazine oxalate Ethyl chloroformate (0.36 g) was added slowly to a stirred solution of 6,7-dimethoxy-1-[4-(N-methylamino)piperidino]phthalazine (1.0 g) and triethylamine (0.9 ml) in dry chloroform (20 ml) at 5°, then the reaction mixture was stirred at room temperature for 18 hours. Thin layer chromatography showed that reaction was incomplete and so additional triethylamine (0.45 ml) and ethyl chloroformate (200 mg) were added at room temperature and stirring was continued for a further 72 hours. The reaction mixture was then shaken with 2 N hydrochloric acid (15 ml), the chloroform phase washed with 2 N sodium hydroxide (20 ml), dried (MgSO$_4$) and concentrated in vacuo.

The residual yellow oil was dissolved in the minimum volume of ether, filtered, concentrated in vacuo, then the residue dissolved in the minimum volume of ethyl acetate and acidified to pH 4 with a solution of oxalic acid in ethyl acetate. The pale yellow oxalate salt was collected and crystallized from ethanol, then acetonitrile, to give 6,7-dimethoxy-1-[4-(N-ethoxycarbonyl-N-methylamino)piperidino]phthalazine mono-oxalate (540 mg), m.p. 206°–209°.

Analysis %: Found: C, 54.5; H, 6.5; N, 12.5 Calculated for $C_{19}H_{26}N_4O.C_2H_2O_4$: C, 54.3; H, 6.1; N, 12.1.

EXAMPLE 38

6,7-Dimethoxy-1-[4-(N-benzyloxycarbonyl-N-methylamino)piperidino]phthalazine hydrochloride hemihydrate, m.p. 235°, was prepared similarly to the previous Example, using benzylchloroformate, 6,7-dimethoxy-1-[4-(N-methylamino)piperidino]phthalazine, followed by ethereal hydrogen chloride.

Analysis %: Found: C, 59.5; H, 6.2; N, 11.2 Calculated for $C_{24}H_{28}N_4O_4.HCl.\frac{1}{2}H_2O$: C, 59.8; H, 6.3; N, 11.6

EXAMPLE 39

Preparation of
6,7-Dimethoxy-1-[4-(N-n-propylcarbamoyloxy)-piperidino]phthalazine hydrochloride 6,7-Dimethoxy-1-[4-hydroxypiperidino]phthalazine (0.81 g), n-propyl isocyanate (0.83 g), triethylamine (0.4 ml) and dry chloroform (20 ml) were heated together under reflux for 10 hours. The mixture was then cooled, treated with water (15 ml) and separated. The chloroform layer was shaken with 1 N sodium hydroxide (10 ml), dried (MgSO$_4$) and evaporated in vacuo to give a yellow oil. The oil was dissolved in the minimum volume of chloroform and chromatographed on silica (bed size 3×27 cm). Elution was commenced with chloroform containing gradually increasing amounts of methanol (up to 10%). The first 800 mls of eluant were discarded then 14×70 ml fractions were collected. Appropriate fractions were selected by thin layer chromatography, combined and evaporated in vacuo to give a yellow oil. This oil was dissolved in the minimum volume of ethyl acetate, diluted with ether (30 ml), and acidified to pH 3 with saturated hydrogen chloride. The precipitated solid was collected and recrystallized from acetonitrile to give 6,7-dimethoxy-1-[4-(N-n-propylcarbamoyloxy)piperidino]phthalazine hydrochloride (0.32 g), m.p. 175°–180°.

Analysis %: Found: C, 55.3; H, 6.5; N, 13.8 Required for $C_{19}H_{26}N_4O_4.HCl$: C, 55.5; H, 6.6; N, 13.6.

EXAMPLES 40–43

The following phthalazines were prepared similarly to Example 39, starting from 1-4-hydroxypiperidino)-6,7-dimethoxy-phthalazine and the appropriate isocyanate:

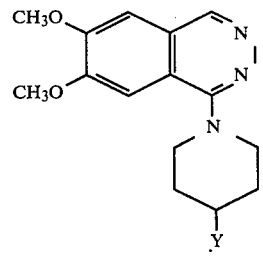

| Example No. | Y | Form Isolated and m.p. (°C.) | Analysis % (Theoretical in brackets) | | |
|---|---|---|---|---|---|
| | | | C | H | N |
| 40 | —OCONHCH₃ | hydrochloride hemihydrate. | 51.8 (52.1 | 6.0 6.2 | 13.9 14.3) |
| 41 | —OCONHCH₂ . (Phenyl) | Free base, 160–162° | 65.6 (65.4 | 6.3 6.2 | 13.4 13.3) |
| 42 | —OCONH . Phenyl | Free base 1 hydrate, 4 186–189° | 63.9 (64.0 | 5.9 6.0 | 13.7 13.6 |
| 43 | —OCONH . (3-pyridyl) | Free base, 213–215° | 61.0 (61.6 | 5.7 5.7 | 17.2 17.1) |

EXAMPLE 44

Preparation of 1-(4-Acetoxypiperidino)-6,7-dimethoxyphthalalazine oxalate 1-(4-Hydroxypiperidino)-6,7-dimethoxyphthalazine (1.45 g), (prepared as in Example 2), acetic anhydride (1.5 g) and acetic acid (12 ml) were heated together at 90° for 17 hours. The cooled solution was then diluted with water (20 ml), basified with sodium carbonate to pH 10, and extracted with chloroform (2×50 ml). The chloroform extract was washed (H₂O), dried (MgSO₄), and evaporated in vacuo to give a dark oil. The oil was applied to the top of a column of powdered silica (bed size 30×2.0 cm) and eluted with chloroform containing increasing percentages (up to 30%) of methanol. Of fifteen fractions (each of 100 ml) collected, fractions 11–13 were combined and evaporated in vacuo to give an oily residue which was triturated with ether (60 ml). After removing insoluble material by filtration, the ethereal solution was treated with ethereal oxalic acid to pH 4 to precipitate the gelatinous oxalate salt. Recrystallization from ethanol gave pink crystals of 1-(4-acetoxypiperidino)-6,7-dimethoxy phthalazine monooxalate (120 mg), m.p. 212°–13°.

Analysis %: Found: C, 54.1; H, 5.5; N. 9.9 Calculated for $C_{17}H_{21}N_3O_4.C_2H_2O_4$: C, 54.2; H, 5.5; N, 10.0.

EXAMPLE 45

Preparation of 6,7-Dimethoxy-1-[4-(2-hydroxypropylpiperidino]phthalazine 6,7-Dimethoxy-1-[4-(2-acetoxypropyl)piperidino]phthalazine (1 g) was heated at 90° in a mixture of 5 N sodium hydroxide (5 ml) and ethanol (5 ml) for 30 hours. The mixture was then evaporated in vacuo and the residue suspended in water (25 ml) from which it was extracted with chloroform (2×25 ml). The combined chloroform extracts were washed with water (20 ml) and evaporated in vacuo to give a crude oily product, which solidified on trituration with ether (20 ml). Recrystallization from acetonitrile gave 6,7-dimethoxy-1-[4-(2-hydroxypropyl)piperidino]phthalazine (400 mg), m.p. 154°–6°.

Analysis %: Found: C, 65.2; H, 7.6; N, 12.6: Required for $C_{18}H_{25}N_3O_3$: C, 65.2; H, 7.6; N, 12.7.

EXAMPLE 46

Preparation of 6,7-Dimethoxy-1-[4-Acetonylpiperidino]phthalazine hydrochloride 6,7-Dimethoxy-1-[4-(2-hydroxypropyl)-piperidino]phthalazine (1.7 g) was added to a stirred mixture of chromium trioxide (50 mesh, 3.5 g), dry methylene chloride (90 ml) and dry pyridine (5.5 g). The mixture was stirred under nitrogen for 3 hours then a large excess of 0.880 ammonia was added, and the reaction mixture was stirred for a further 2 hours. Suspended chromium salts were removed by passing the organic layer down a short column of silica and then by filtration through "Hyflo" (Trade Mark) covered with a layer of charcoal (0.5 cm). Evaporation of the clear solution in vacuo gave the oxidation product as a straw-colored oil which was redissolved in the minimum quantity of ethyl acetate and treated with excess ethereal hydrogen chloride to precipitate the hydrochloride salt. Recrystallization of the salt from ethanol gave 6,7-dimethoxy-1-[4-acetonylpiperidino]phthalazine hydrochloride (0.5 g), m.p. 213°–14°.

Analysis %: Found: C, 58.4; H, 6.7; N, 11.2: Required for $C_{18}H_{23}N_3O_3.HCl$: C, 59.1; H, 6.6; N, 11.5.

The following Preparations, in which all temperatures are in °C., illustrate the preparation of certain of the intermediates used in the Examples. In most cases these intermediates were used directly in the Examples without further characterization:

Preparation 1

A. Preparation of N-(1-Benzyl-piperid-4-yl)-N-methyltrifluoracetamide hydrochloride Trifluoracetic anhydride (34.7 g) was added dropwise to a cooled, stirred mixture of 1-benzyl-4-(N-methylamino)piperidine (30 g), triethylamine (41.5 ml) and dry toluene (170 ml). The mixture was then allowed to stand at room temperature overnight, followed by treatment with water (200 ml) and separation of the toluene layer, which was then dried ($Na_2CO_3$) and evaporated in vacuo to give an oil. The oil was dissolved in the minimum quantity of ether and acidified with excess ethereral hydrogen chloride to precipitate the hydrochloride salt of N-(1-benzyl-piperid-4-yl)-N-methyltrifluoracetamide (48 g), m.p. 265°–268°, structure verified by i.r. and n.m.r. spectroscopy.

B. Preparation of N-(Piperid-4-yl)-N-methyltrifluoroacetamide hydrochloride

The hydrochloride salt prepared in A above (48 g) was dissolved in a mixture of ethanol (500 ml) and water (50 ml) and hydrogenated at 20°/50° p.s.i. over a palladium-charcoal catalyst until hydrogen uptake ceased. The catalyst was removed by filtration and the filtrate evaporated to in vacuo. The resulting green solid was recrystallized from isopropanol to give N-(piperid-4-yl)-N-methyltrifluoroacetamide hydrochloride (23 g), m.p. 255°–257°; structure verified by i.r. and n.m.r. spectroscopy.

C. Preparation of 6,7-Dimethoxy-1-[4-(N-methyltrifluoracetamido piperidino]phthalazine 1-Chloro-6,7-dimethoxyphthalazine (4.5 g), N-(piperid-4-yl)-N-methyltrifluoracetamide hydrochloride (9.9 g) and triethylamine (5.5 ml) were heated together for 5 hours at 100° in iso-amylalcohol (100 ml). The solution was cooled to room temperature and the excess iso-amylalcohol was removed by distillation in vacuo. The residue was dissolved in dilute hydrochloric acid to pH 2, extracted with chloroform (2×100 ml), the chloroform extract shaken with dilute sodium hydroxide, and then quickly separated. The organic phase was washed with water (150 ml), dried over magnesium sulphate, and taken to dryness in vacuo. The resultant brown oil was triturated with ether, filtered, and the filtrate was left standing at room temperature for two hours, during which time a yellow solid precipitated from solution. This solid was collected and crystallized from isopropylalcohol, yielding 6,7-dimethoxy-1-[4-(N-methyltrifluoracetamido)piperidino]phthalazine (2.9 g), m.p. 150°–152°.

Analysis %: Found: C, 54.3; H, 5.4; N, 13.7: Calculated for $C_{18}H_{21}N_4O_3F_3$: C, 54.3; H, 5.3; N, 14.1.

D. Preparation of 6,7-Dimethoxy-1-[4-(N-methylamino)piperphthalazine 6,7-Dimethoxy-1-[4-(N-methyltrifluoroacetamido) piperidino]phthalazine (0.6 g) was heated at 95°, with stirring, in tetrahydrofuran (5 ml) and 5 N sodium hydroxide (2.5 ml). The mixture was then cooled to room temperature, concentrated to a small volume in vacuo, and shaken with chloroform (15 ml) and water (15 ml). The organic phase was separated, washed with water (10 ml), and dried over magnesium sulphate. The chloroform was removed in vacuo and the residual yellow oil was converted to its oxalate salt by treatment with a solution of oxalic acid in iso-propylalcohol. Recrystallization from methanol gave yellow crystals of 6,7-dimethoxy-1-[4-(N-methylamino)piperidino] phthalazine sesquioxalate hemihydrate (0.3 g), m.p. 194°–196°.

Analysis %: Found: C, 51.6; H, 5.8; N, 12.6: Calculated for $C_{16}H_{22}N_4O_2:3/2(COOH):\frac{1}{2}H_2O$: C, 51.1; H, 5.9; N, 12.6.

Preparation 2

(This is an alternative to the previous Preparation)

A. Preparation of 1-[6,7-Dimethoxyphthalazin-1-yl]piperid-4-one trimethylene ketal 4-Piperidone trimethylene ketal hydrochloride (20 g), 1-chloro-6,7-dimethoxyphthalazine (10 g), triethylamine (50 ml) and ethanol (300 ml) were heated together under reflux for 70 hours. The resulting mixture was evaporated in vacuo and the residue was partitioned between chloroform (2×100 ml) and water (60 ml). The chloroform extracts were combined, dried ($MgSO_4$) and evaporated in vacuo to give a crude brown oil which on trituration with ethyl acetate (100 ml) at boiling point gave 1-[6,7-dimethoxyphthalazin-1-yl]piperid-4-one trimethylene ketal (11 g), m.p. 194°–6°. A second crop of the product (3 g) was obtained by evaporating the ethyl acetate trituration liquors.

B. Preparation of 6,7-Dimethoxy-1-[4-oxopiperidino]phthalazine

1-[6,7-Dimethoxyphthalazin-1-yl]piperid-4-one trimethylene ketal (14 g) was stirred for 4 hours in simulated gastric medium* (1 liter) at 45°. Anhydrous sodium carbonate (12 g) was added cautiously to the solution followed by sodium chloride until saturated. The solution was extracted with chloroform (200 ml, plus 5×50 ml), the combined extracts dried ($Na_2CO_3$) and evaporated to give the crude product as an ochre powder (11.6 g). Recrystallization of a sample from methanol (twice) gave 6,7-dimethoxy-1-[4-oxopiperidino]phthalazine as buff-colored needles, m.p. 180°–181°.

Analysis %: Found: C, 62.4; H, 5.9; N, 14.2: Required for $C_{15}H_{17}N_3O_3$: C, 62.7; H, 6.0; N, 14.6.

*[prepared by dissolving NaCl (2 g) and concentrated HCl (7 ml) in water (to 1 liter)].

C. Preparation of 6,7-Dimethoxy-1-[4-(N-methylamino) piperidino]phthalazine oxalate To 6,7-Dimethoxy-1-(4-oxopiperidino)phthalazine (11 g), methylamine hydrochloride (4.7 g) and potassium hydroxide flakes (1.1 g) in a methanol (200 ml) suspension was added sodium cyanoborohydride (1 g) in methanol (20 ml). The resulting mixture was stirred for 20 hours, after which a further portion of sodium cyanoborohydride (0.2 g) was added. After stirring for an additional 4 hours the mixture was treated with potassium hydroxide flakes (4 g) and evaporated in vacuo. The residue was partitioned between methylenechloride-2 N NaOH (20:10 ml), and the methylene chloride layer was washed with brine, dried ($Na_2CO_3$) and evaporated. The crude product was dissolved in the minimum quantity of methyl alcohol and treated with saturated methanolic oxalic acid to precipitate the oxalate salt. Recrystallization from methanol gave 6,7-dimethoxy-1-[4-(N-methylamino)piperidino]phthalazine oxalate (9 g).

Preparation 3

A. Preparation of 6,7-Dimethoxyphthalazine-1-one 4,5-Dimethoxyphthaladehydic acid (10 g) and hydrazine hydrate (2.4 ml) in ethanol (150 ml) were heated under reflux for 20 hours during which time a white crystalline solid formed. The mixture was cooled in an ice bath, filtered and the resulting product dried to give crude 6,7-dimethoxyphthalzin-1-one (7 g). A sample was crystallized from water yielding colorless needles, m.p. 254°–256°.

Analysis %: Found: C, 58.4; H, 4.8; N, 13.9: Calculated for $C_{10}H_{10}N_2O_3$: C, 58.3; H, 4.9; N, 13.6.

B. Preparation of 1-Chloro-6,7-dimethoxyphthalazine 6,7-Dimethoxyphthalazin-1-one (20.6 g) was heated under reflux with phosphoryl chloride (200 ml) for 6 hours then cooled to room temperature and the excess phosphoryl chloride removed under reduced pressure. The resultant brown solid was suspended in acetone (150 ml) and poured onto cold (5°) concentrated ammonium hydroxide (200 ml).

The crude product was filtered, washed with water (200 ml) then petroleum ether (200 ml). The pale yellow solid was dried (20 g), dissolved in the minimum volume of chloroform and precipitated with excess petroleum ether, after which it was recovered by filtration, washed again with petroleum ether (100 ml) and dried to give 1-chloro-6,7-dimethoxyphthalazine (13 g), m.p. 195°–197° with decomposition.

Analysis %: Found: C, 53.3; H, 4.2; N, 12.7: Calculated for $C_{10}H_9ClN_2O_2$: C, 53.5; H, 4.0; N, 12.5.

Preparation 4

A. Preparation of N-Acetyl-4-allyloxypiperidine

A solution of N-acetyl-4-hydroxypiperidine (100 g) in dimethylformamide (250 ml) was added dropwise to sodium hydride (38 g, 50% mineral oil dispersion) under an atomsphere of nitrogen. The mixture was stirred for 2 hours then allyl bromide (93 g) was added slowly while maintaining the reaction temperature at 25° by external cooling. The mixture was then stirred at room temperature overnight, diluted with isopropanol (20 ml) and ether (500 ml), filtered, and evaporated in vacuo. Distillation of the residue gave N-acetyl-4-allyloxypiperidine (108.8 g), b.p. 128°/2 mm, identified spectroscopically.

B. Preparation of 4-(2-Ethoxy-n-propoxy)piperidine

A solution of N-acetyl-4-allyloxypiperidine (6.4 g) in absolute ethanol (10 ml) was added dropwise to a stirred suspension of mercuric acetate (11.5 g) in ethanol (50 ml) at room temperature.

After 20 minutes the mercuric acetate had dissolved and the mixture was stirred for a further 40 minutes, cooled in ice-water, and sodium hydroxide (20 ml, 5 N) was then added, the mixture stirred for 10 minutes, and acetic acid added to bring the pH to 6. The mixture was filtered from precipitated mercury, the ethanol evaporated in vacuo, and the resulting aqueous phase extracted with chloroform. The organic extracts were dried ($Na_2SO_4$), evaporated in vacuo, and the resulting crude residue (7.5 g) taken up in ethanol (50 ml) and heated under reflux overnight with sodium hydroxide (20 ml, 5 N) and water (20 ml). Most of the ethanol was then removed in vacuo, the aqueous layer extracted with ether, the extracts dried ($Na_2SO_4$) and evaporated to leave a residue (5 g). Thin layer chromatography indicated incomplete hydrolysis of the acetyl function had occurred so the residue was treated with hydrochloric acid (20 ml, 2 N) and heated on a steam bath for 10 hours. The mixture was then washed with ether, the aqueous phase basified ($NaCO_3$), extracted with ether and the organic extract dried ($Na_2SO_4$) and evaporated to leave a residue (4.3 g). Distillation of the residue gave 4-(2-ethoxy-n-propoxy)piperidine (3.0 g), b.p. 112°–116°/10 mm, from which the sesquioxalate salt was prepared by reacting an ethereal solution of the piperidine with etheral oxalic acid, followed by recrystallization from ethyl acetate, the oxalate having an m.p. of 68°–70°.

Analysis %: Found: C, 48.3; H, 7.5; N, 4.7: Calculated for $C_{10}H_{21}NO_2.1.5(CO_2H)_2$: C, 48.4; H, 7.5; N, 4.4.

Preparation 5

Preparation of 4-(2-Hydroxy-n-propoxy)piperidine

N-acetyl-4-allyloxypiperidine (18 g) in tetrahydrofuran (30 ml) was added dropwise to a stirred yellow suspension of mercuric acetate (34 g) in a mixture of water (120 ml) and tetrahydrofuran (120 ml). The suspension dissolved during the addition and the resulting clear solution was stirred at room temperature for 20 minutes, then sodium hydroxide (70 ml, 5 N) was added, accompanied by ice/water cooling. The intermediate thus obtained was then reduced by the addition of sodium borohydride (2 g) in sodium hydroxide (40 ml, 5 N), the excess hydride being destroyed after 10 minutes with glacial acetic acid. The liquid phase was then decanted off, saturated with sodium chloride, the organic phase separated, and the remaining aqueous layer extracted four times with chloroform. The combined organic phases were dried ($Na_2SO_4$), and evaporated in vacuo to leave a colorless oil (23 g).

This oil was stirred with 5 N sodium hydroxide at room temperature for 16 hours, then at 100° for 2 hours. The solution was then extracted with chloroform (four times), the combined extracts dried ($Na_2SO_4$), and evaporated in vacuo to leave a crude crystalline product (1.6 g). This was taken up in methylene chloride, filtered, evaporated, and the residue triturated with petroleum ether (40°/60°) to yield 4-(2-hydroxy-n-propoxy)piperidine (11.0 g), m.p. 55°–57°. The oxalate salt thereof was prepared as in Preparation 4(B) and recrystallized from isopropanol, m.p. 104°–105°.

Analysis %: Found: C, 48.2; H, 7.7; N, 5.6: Calculated for $C_8H_{17}NO_2.(CO_2H)_2$: C, 48.2; H, 7.7; N, 5.6.

Preparation 6

A. Preparation of N-acetyl-4-(2-methylallyloxy)piperidine

This compound was prepared similarly to Preparation 4(A), starting from N-acetyl-4-hydroxypiperidine and 2-methylallyl chloride, and was distilled and used directly in the next stage. It had a b.p. of 128° at 1 mm.

B. Preparation of 4-(2-hydroxy-2-methyl-n-propoxy)piperidine

This compound, m.p. 80°–82°, was prepared similarly to Preparation 5, starting from N-acetyl-4-(2-methylallyloxy)piperidine and mercuric acetate in a mixture of water and tetrahydrofuran.

Analysis %: Found: C, 62.2; H, 11.1; N, 8.3: Calculated for $C_9H_{19}NO_2$: C, 62.4; H, 11.1; N, 8.1.

Preparation 7

Preparation of N-methyl-N-(piperid-4-yl)benzamide

1-Benzyl-4-(methylamino)piperidine dihydrochloride (7 g) in dry chloroform (50 ml) with triethylamine (10 ml) was stirred and cooled while benzoyl chloride (3 ml) was added slowly. The mixture was then refluxed for 5 hours followed by evaporation in vacuo to give a mixture containing crude N-(1-benzylpiperid-4-yl)-N-methyl-benzamide hydrochloride (7.5 g).

This hydrochloride was dissolved in glacial acetic acid (60 ml) and hydrogenated over a 30% palladium on charcoal catalyst at 50°/50 p.s.i. until uptake of hydrogen ceased. The catalyst was then removed by filtration and the filtrate basified to pH 10 ($Na_2CO_3$) followed by extraction with chloroform. The chloroform extract was dried ($Na_2CO_3$) and evaporated to give crude N-methyl-N-(piperid-4-yl)benzamide (3.4 g) as a clear oil, with an n.m.r. spectrum consistent with this structure.

Preparation 8

Preparation of 4-n-Butyramidopiperidine hydrochloride

4-Amino-1-benzylpiperidine dihydrochloride (7.4 g) in dry chloroform (75 ml) was cooled to 0°–10° and treated dropwise with triethylamine (16.6 ml). n-Butyric anhydride (4.7 g) was added slowly to the cooled solution, then the mixture was kept at 0°–5° for 15 minutes and at room temperature for 1 hour. Water (80 ml) was added and the chloroform phase separated, washed with 10% aqueous sodium hydroxide (50 ml) then with water (50 ml), dried ($MgSO_4$) and evaporated in vacuo to give crude crystalline 4-n-butyramido-1-benzylpiperidine (6.5 g). This was dissolved in ethanol (65 ml) containing 2 N hydrochloric acid (5 ml) and hydrogenated over a palladium on charcoal catalyst at 50°/50 p.s.i. until uptake of hydrogen ceased. The catalyst was removed by filtration and the ethanol was removed by distillation in vacuo. The residue was re-dissolved in water (60 ml) and extracted with chloroform (3×50 ml). The aqueous phase was treated with acetic acid to pH 3 and evaporated in vacuo. The residue was dissolved in ethanol (60 ml), filtered and re-evaporated in vacuo to give a colorless oil which solidified. After trituration with ether (100 ml), crude deliquescent 4-n-butyramidopiperidine hydrochloride (m.p. 141°–3°) (4.2 g) was recovered by filtration.

Preparation 9

Preparation of 1-(Piperid-4-yl)-1,3,3-trimethylurea

Dimethylcarbamoyl chloride (2.7 g) was added slowly to a stirred, cooled solution of 1-benzyl-4-(methylamino)piperidine dihydrochloride (7 g) in dry chloroform (50 ml) and triethylamine (7.7 g). The mixture was then stirred at room temperature for 3 hours and heated under reflux for a further 7 hours. The cooled mixture was treated with water (50 ml), separated, and the chloroform layer dried ($MgSO_4$) and evaporated in vacuo to give 1-(1-Benzylpiperid-4yl)-1,3,3-trimethyl urea (6.5 g) as a mobile oil.

This oil was dissolved in glacial acetic acid (60 ml), and hydrogenated over 30% palladium on charcoal at ambient temperature/50 p.s.i. until uptake of hydrogen ceased. The catalyst was then removed by filtration and the filtrate evaporated to dryness in vacuo. The residue was basified to pH 10 ($Na_2CO_3$), extracted with chloroform, and the chloroform extract dried ($Na_2CO_3$) and evaporated in vacuo to give 1-(piperid-4-yl)-1,3,3-trimethyl urea (1.6 g) as a gum with n.m.r. spectrum consistent with this structure.

Preparation 10

A. Preparation of 1-Acetyl-4-methylaminopiperidine hydrochloride

Potassium hydroxide flakes (2 g) were added to a solution of methylammonium chloride (8.5 g) in methanol (75 ml) at 0°–5°. 1-Acetylpiperid-4-one (14 g) was then added, the mixture stirred for 15 minutes and then a solution of sodium cyanoborohydride (2.5 g) in methanol (25 ml) was added over a period of 30 minutes. The mixture was stirred at room temperature overnight and then potassium hydroxide (6 g) was added. After filtration through sodium carbonate, the filtrate was evaporated to dryness and the residue was partitioned between chloroform (100 ml) and aqueous potassium hydroxide (2.5 g in 15 ml $H_2O$). The chloroform layer was dried ($Na_2CO_3$) and evaporated to give a colorless oil which was dissolved in a mixture of ethanol (40 ml) and isopropyl alcohol (40 ml), then excess hydrogen chloride gas was bubbled into the cooled solution (ice bath). Addition of acetone resulted in the slow crystallization of 1-acetyl-4-methylaminopiperidine hydrochloride (5.5 g) (identified by n.m.r.).

B. Preparation of N-Methyl-N-(piperid-4-yl)methanesulphonamide

1-Acetyl-4-methylaminopiperidine (5.5 g) and triethylamine (6 ml) were stirred together at room temperature in dry chloroform (100 ml) while methanesulphonyl chloride (5 g) was added slowly. The mixture was stirred overnight at ambient temperature, then 5 N sodium hydroxide solution (30 ml) was added. The chloroform layer was separated, dried ($Na_2CO_3$) and evaporated in vacuo to give a crude product.

Recrystallization from a mixture of methanol/ethyl acetate (1:10) gave 1-acetyl-4-(N-methyl-methansulphonamido)piperidine (5.5 g), m.p. 132°.

This product (5 g) was heated under reflux for 1½ hours in a mixture of ethanol (20 ml) and 5 N sodium hydroxide (50 ml). The ethanol was then removed in vacuo to precipitate the product as a white solid, which was recovered by filtration. The solid was extracted with a mixture of chloroform and ethanol (10:1 ) (2×60 ml) after which the extract was dried ($Na_2CO_3$) and evaporated in vacuo to give crude N-methyl-N-(piperid-4-yl)methane sulphonamide (5.2 g). This was used directly. (The infra-red spectrum showed complete deacylation).

Preparations 11 to 15

The following sulphonamides were prepared similarly to the previous Preparation, using the appropriate sulphonyl chloride in place of methanesulphonyl chloride:-

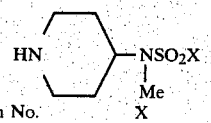

| Preparation No. | X |
| --- | --- |
| 11 | n-propyl |
| 12 | 3,4-dimethylphenyl |
| 13 | benzyl |
| 14 | phenyl |

-continued

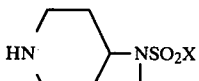

| Preparation No. | X |
|---|---|
| 15 | 3-pyridyl |

These intermediates were used directly without further purification.

Preparation 16

Preparation of N-(Piperid-4-yl)methansulphonamide hydrochloride

Methanesulphonyl chloride (2.5 g) was added dropwise to a stirred solution of 1-benzyl-4-aminopiperidine (4 g) and triethylamine (4 ml) in chloroform (40 ml) at room temperature. After 20 minutes, water (40 ml) was added, the organic layer separated, dried (MgSO₄), and evaporated in vacuo to give an oil which crystallized from ether to give N-(1-benzylpiperid-4-yl)methanesulphonamide (2 g, m.p. 135°-6°).

The above product (2 g), dissolved in a mixture of ethanol (50 ml) water (20 ml) and concentrated hydrochloric acid (15 ml), was hydrogenated over 10% palladium on carbon at 20°/40 p.s.i. until uptake of hydrogen ceased. After removal of the catalyst by filtration, the ethanol was evaporated in vacuo to give crude N-(piperid-4-yl) methanesulphonamide hydrochloride. Residual water was removed by azeotroping with toluene and the product was then utilized without further purification.

Preparation 17

A. 3-n-Butyl-1-(4-pyridyl)urea

A solution of n-butylisocyanate (34.0 g) in dimethylformaide (DMF) (60 ml) was added dropwise over 25 minutes to a stirred solution of 4-aminopyridine (28.0 g) in DMF (190 ml), and the resulting mixture was heated at 65°-70° for 1½ hours. After cooling overnight, further n-butylisocyanate (3 ml) was added, and the mixture heated at 70° for 3 hours.

The resulting solution was then evaporated to leave an orange oil which was taken up in ethyl acetate (500 ml), treated with dry hydrogen chloride gas and the crude product (59.5 g) collected. Recrystallization of the crude product from ethyl acetate/methanol gave 3-n-butyl-1-(4-pyridyl)urea hydrochloride (35.5 g), m.p. 199°-202°.

Analysis %: Found: C, 51.99, H, 6.87; N, 18.27: C₁₀H₁₅N₃O.HCl requires: C, 52.28; H, 7.02; N, 18.29.

A further 13.6 g of the product, m.p. 198°-201° was recovered from the crystallization of the mother liquor.

B. 3-n-Butyl-1-(4-piperidyl)urea

A solution of 3-n-butyl-1-(4-pyridyl)urea hydrochloride (37.4 g) in ethanol-water (1:1, 400 ml) containing 5% rhodium/alumina catalyst (10 g) was hydrogenated (50°, 750 psi) until no further uptake of hydrogen occurred. The catalyst was then removed by filtration and the solvent evaporated to leave an oil which partially solidified on storage at 0°. The solid was separated, treated with base, extracted with chloroform/n-butanol, the extracts evaporated and the residue recrystallized twice from ethyl acetate to give 3-n-butyl-1-(4-piperidyl)urea, (6.3 g), m.p. 132°-134°.

Analysis %: Found: C, 59.86; H, 10.93; N, 20.78: C₁₀H₂₁N₃O requires: C, 60.26; H, 10.62; N, 21.08.

Preparation 18

3-n-Propyl-1-methyl-1-(4-piperidyl)urea 4-(N-methylamino)-1-benzylpiperidine dihydrochloride (41.4 g) (prepared as in German Offenlegungsschrift No. 2341376), triethylamine (30.2 g) and n-propylisocyanate (12.7 g) in chloroform (200 ml) were mixed together then allowed to stand overnight. The resulting solution was then washed with water (3×100 ml), and, after separation, the chloroform layer was dried and evaporated to leave an oil which on crystallization from petrol (b.p. 60°-80°) gave, 3-n-propyl-1-methyl-1-(1-benzyl-4-piperidyl)urea (42.0 g), m.p. 84°-86°.

Analysis %: Found: C, 70.3; H, 9.5; N, 14.6: C₁₇H₂₇N₃O requires: C, 70.6; H, 9.4; N, 14.5.

The above N-n-propyl benzyl derivative (42.0 g) in 50% aqueous acetic acid with Pd/C catalyst (5 g) was hydrogenated at room temperature/50 p.s.i. The catalyst was filtered off, the solution basified, evaporated and the residue extracted with chloroform. The extracts were dried then evaporated to give 3-n-propyl-1-methyl-2-(4-piperidyl)urea (27.0 g) as an oil, characterized spectroscopically. The hydrochloride salt melted at 201°-8°.

Analysis %: Found: C, 50.8; H, 9.3; N, 17.8: C₁₀H₂₁N₃O.HCl requires: C, 50.9; H, 9.4; N, 17.8.

Preparation 19

A. Preparation of Methyl-3-[1-acetylpiperid-4-yl]propionate

Methyl 3-[piperid-4-yl]propionate (11 g) and acetic anhydride (35 ml) were heated together on a steam bath for 1 hour. The mixture was cooled and methanol (50 ml) was added to destroy excess anhydride. The solution was evaporated to dryness in vacuo and the residue was partitioned between chloroform (200 ml) and 2 N hydrochloric acid (100 ml) dried (Na₂CO₃) and evaporated to give methyl 3-[1-acetyl-piperid-4-yl]propionate (13 g) as an oil.

B. Preparation of 3-(piperid-4-yl)-1,1-dimethyl propanol

Crude methyl 3-(1-acetyl-piperid-4-yl)propionate (13 g) in dry ether (80 ml) was added dropwise, at 0°-10°, to methyl magnesium iodide [prepared from Mg (8 g) and methyliodide (40 g)] in dry ether (150 ml). The mixture was then stirred at room temperature (20°) overnight, after which time the resulting complex was decomposed by the addition of saturated, aqueous ammonium chloride (50 ml). Dilute hydrochloric acid was added until all the solids dissolved (pH 7-8) and then the ether layer was separated. The aqueous layer was extracted with ether (200 ml) and chloroform (200 ml) and the combined organic extracts were washed with 2 N hydrochloric acid (100 ml) and then with brine (50 ml). After drying (Na₂CO₃), the organic solvents were removed in vacuo to give 3-(1-acetyl-piperid-4-yl)-1,1-dimethyl propanol as a crude oil.

Further material was obtained by basifying the original aqueous layer and the acidic washings, and extracting with chloroform. (Total yield, 5 g). De-acylation was achieved by heating the above compound (2 g) for 1 hour under reflux with a mixture of methanol and 2 N sodium hydroxide solution [2:1 (30 ml)]. The methanol was evaporated in vacuo and the residue extracted with chloroform (2×20 ml). The extract was dried (Na₂CO₃) and evaporated in vacuo to give crude 3-(piperid-4-yl)-1,1-dimethyl propanol (4.5 g) as an oil.

Preparation 20

4-(Piperid-4-yl)-1,1-dimethylbutanol was prepared basically similarly to Part B of the previous Preparation, but by the reaction of methyl 4-(pyrid-4-yl)butyrate and methyl magnesium iodide, followed by hydrogenation in place of de-acylation.

Preparation 21

A. Preparation of Methyl Ester of 3-(piperid-4-yl)propionic acid

Diethyl malonate (50 g), 4-pyridylaldehyde (30 g) and 1-methylpiperazine (4 ml) were heated overnight under reflux in toluene (200 ml), utilizing a Dean and Stark water trap. The toluene was then removed in vacuo and the residue distilled to give ethyl 2-ethoxy-carbonyl-3-(pyrid-4-yl) acrylate, b.p. 140°–150°/1.5 mm, (35 g). Hydrogenation of this in glacial acetic acid (600 ml) over platinum oxide at 60°/60 p.s.i. until hydrogen uptake ceased gave, after removal of catalyst and solvent, the crude acetate salt of diethyl 2-(piperid-4-yl-methyl)malonate, which was then heated overnight, under reflux, with concentrated hydrochloric acid (500 ml) to give, on evaporation to dryness, 3-(piperid-4-yl)propionic acid hydrochloride.

Conversion to the methyl ester was achieved by dissolving the crude acid hydrochloride in methyl alcohol (600 ml), and adding thionyl chloride (200 ml) cautiously, dropwise. On completion of the addition the mixture was heated under reflux for 3½ hours, evaporated to dryness, basified with 2 N sodium hydroxide (to pH 12), and extracted with chloroform (2×200 ml).

The crude ester was obtained by evaporation of the dried chloroform extract. (Yield of methyl ester=14 g).

B. Preparation of N-n-Propyl-2-(piperid-4-yl)acetamide

Methyl 2-(pyrid-4-yl)acetate (10 g), n-propylamine (30 ml) and 3 A molecular sieves (10 g) were heated together at 100° for 148 hours in a stainless steel bomb. Excess amine and molecular sieves were removed and the crude product in glacial acetic acid (100 ml) was hydrogenated over platinum oxide catalyst at 30°/50° p.s.i. until uptake of hydrogen ceased. The catalyst was removed by filtration, the excess acetic acid distilled off in vacuo, and the residue basified with aqueous sodium bicarbonate and extracted with ethyl acetate (100 ml). The organic layer was dried (MgSO₄) and evaporated in vacuo to give crude N-n-propyl-2-(piperid-4-yl)acetamide as an oil. This was utilized without further purification.

Preparation 22

N-methyl-2-(piperid-4-yl)acetamide was prepared similarly to the previous preparation, using methylamine in place of n-propylamine.

Preparation 23

Preparation of N-Methyl-3-(piperid)-4-yl)propionamide

Ethyl 3-(piperid-4-yl)propionate (7 g) (prepared similarly to Preparation 21 A using ethyl alcohol in place of methyl alcohol) was dissolved in ethanolic methylamine (33%, 50 ml) and heated in a stainless steel bomb for 6 hours at 120°. The mixture was then evaporated to dryness in vacuo and the residue partitioned between 2 N NaOH (20 ml) and chloroform (40 ml). The chloroform layer was dried (Na₂CO₃) and evaporated to give N-methyl-3-(piperid-4-yl)propionamide (6 g) as a crude oil.

Preparation 24

N,N-dimethyl-3-(piperid-4-yl)propionamide was prepared in a similar manner to the previous Preparation but using dimethylamine in place of methylamine.

Preparation 25

N-n-Propyl-3-(piperid-4-yl)propionamide was prepared similarly to Preparation 23, starting from methyl 3-(piperid-4-yl)propionate and ethanolic n-propylamine.

Preparation 26

Preparation of 4-(piperid-4-yl)butyramide 4-(Pyrid-4-yl)butyric acid hydrochloride (ca. 35 g) in dichloroethane (250 ml) and dimethylformamide (0.5 ml) was treated with thionyl chloride (100 ml). The vigorous exothermic reaction was allowed to subside and then the mixture was heated under reflux for 10 minutes, followed by evaporation to dryness in vacuo to give crude 4-(pyrid-4-yl)butyroyl chloride hydrochloride.

This salt was dissolved in acetone and poured into a mixture of ice and excess concentrated ammonia. The reaction mixture was set aside for 1 hour, then extracted with chloroform, and the extracts dried (Na₂CO₃) and evaporated in vacuo to give crude 4-(pyrid-4-yl)butyramide as a purple solid.

The crude amide was dissolved in glacial acetic acid and hydrogenated at 60°/60 p.s.i. over a platinum oxide catalyst until uptake of hydrogen ceased. The catalyst was removed by filtration and the filtrate was evaporated in vacuo to give crude 4-(piperid-4-yl)butyramide as an oil.

Preparation 27

Preparation of Ethyl 2-(piperid-4-yl)acetate

Triethylphosphonoacetate (66.9 g) in dry dimethoxy ethane (200 ml) was added dropwise to a suspension of sodium hydride (14.4 g) in dimethoxyethane (350 ml) maintained at 6°–8° by external cooling and under an atmosphere of nitrogen. After stirring at ambient temperature for 1 hour a solution of 1-benzylpiperid-4-one (56.7 g) in dimethoxy ethane (250 ml) was added slowly, maintianing the temperature at 17°–19°. The mixture was then allowed to stand for 1 hour, followed by heating under reflux for a further hour, after which it was cooled, poured into water (3000 ml) and extracted with ether (2×150 ml). The ether extract was dried (MgSO₄) and evaporated in vacuo to give a crude oil which on distillation gave ethyl 2-(1-benzyl-piperid-4-ylidene) acetate (34.4 g), b.p. 150–154/0.2 mm.

Hydrogenation in ethanol (170 ml) over a 5% palladium on charcoal catalyst at 40°/40 p.s.i., until uptake of hydrogen ceased, give ethyl 2-(1-benzylpiperid-4-yl)acetate (b.p. 134°–140°/0.3 mm). Removal of the benzyl group was achieved by re-dissolving this product (10.4 g) in a mixture of ethanol (100 ml), 2 N hydrochloric acid (20 ml) and water (10 ml), and hydrogenating at 50°/50 p.s.i. over a 5% palladium on charcoal catalyst. After removal of the catalyst and basification with concentrated ammonia, the mixture was extracted with chloroform (2×100 ml) dried (MgSO₄) and evaporated in vacuo to give crude ethyl 2-(piperid-4-yl)acetate, m.p. 120°–23°.

This was utilized without further purification.

Preparation 28

Preparation of 4-(2-Methoxyethyl)piperidine 4-(2-Methoxyethyl)pyridine (9.6 g), in a mixture of ethanol (100 ml) and 2 N hydrochloric acid (30 ml) was hydrogenated over platinum oxide at 50°/50 p.s.i. until uptake of hydrogen ceased. The catalyst was removed by filtration and the solution evaporated in vacuo. The residue was then dissolved in water (50 ml), basified to pH 8 with dilute sodium hydroxide, and extracted with chloroform. The aqueous phase was evaporated in vacuo to give an oil which solidified on cooling. The solid was triturated with ether (60 ml), collected by filtration and dissolved in the minimum quantity of boiling ethyl acetate. The hot solution was filtered and on cooling deposited hygroscopic crystals of 4-(2-methoxyethyl)piperidine (9.9 g), m.p. 108°–110°. The structure was verified by i.r. and n.m.r. spectroscopy.

Preparations 29 and 30

The following piperidines were prepared similarly to the previous Preparation, starting from the appropriate pyridine.

| Preparation No. | X |
|---|---|
| 29 | —CH₂CH₂OCH(CH₃)₂ |
| 30 | —CH₂C(CH₃)₂OH |

Preparation 31

Preparation of 4-(2-Acetoxypropyl)piperidine hydrochloride 4-(2-Hydroxypropyl)pyridine hydrochloride (11 g) in glacial acetic acid (110 ml) was hydrogenated at 50°/50 p.s.i. over a platinum oxide catalyst until uptake of hydrogen ceased. The catalyst was removed by filtration and the filtrate was evaporated to dryness in vacuo. The residue was triturated with ether (100 ml) and the resultant solid was recrystallized from ethyl acetate-isopropyl alcohol (1:1) to give 4-(2-acetoxypropyl)piperidine hydrochloride (1 g) m.p. 188°–191°.

Analysis %: $C_{10}H_{19}NO_2 \cdot HCl \cdot \frac{1}{4}H_2O$ requires: C, 53.1; H, 9.1; N, 6.2: Found: C, 52.8; H, 9.1; N, 6.3. [A second crop (7 g), m.p. 188°–191° was obtained by concentrating the recrystallization liquors].

Preparation 32

Preparation of 4-(N-Ethylcarbamoyloxy)piperidine

1-Benzyl-piperidin-4-ol (293.4 g), ethyl isocyanate (120 g) and 1,2-dichloroethane (1467 ml) were heated and stirred together under reflux for 7 hours. A further 10.9 g of ethyl isocyanate was then added and refluxing was continued for a further 6 hours. After cooling and standing for 36 hours at room temperature, the reaction had still not proceeded to completion and so a further 33 g of ethyl isocyanate was added and the heating under reflux continued for a further 6 hours.

The mixture was then cooled, poured into water (2000 ml) and stirred for 1½ hours, after which time the organic layer was separated, washed with saturated bicarbonate solution (2000 ml) and water (2000 ml).

The combined aqueous phases were further extracted with dichloroethane (150 ml) and the combined organic phases were dried (MgSO₄) and evaporated in vacuo to give a crude product which was stirred with boiling hexane, cooled and filtered to give 1-benzyl-4-(N-ethylcarbamoyloxy)piperidine (354.4 g), m.p. 96°–98°.

This product (118 g) in industrial methylated spirits (826 ml) was hydrogenated at 50°/50 p.s.i. over a 5% palladium on charcoal catalyst (12 g) until uptake of hydrogen ceased. The catalyst was removed by filtration, the filtrate evaporated in vacuo and the residue recrystallized from a mixture of hexane (450 ml) and ethyl acetate (112 ml) to give 4-(N-ethylcarbamoyloxy)piperidine (208.1 g), m.p. 85°–87°.

What is claimed is:

1. A method of treating congestive heart failure in a human subject having such condition which comprises parenterally administering to said human subject a congestive heart failure treating amount of a compound selected from the group consisting of:

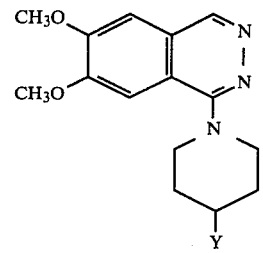

and a pharmaceutically acceptable acid addition salt thereof, wherein Y is selected from the group consisting of —CH₂COR₁ wherein R₁ is alkyl having from one to four carbon atoms or alkoxy having from one to four carbon atoms; —N(R₂)COR₃ wherein R₂ is hydrogen or alkyl having from one to four carbon atoms, and R₃ is alkyl having from one to four carbon atoms, alkoxy having from one to four carbon atoms, phenyl or benzyloxy; —N(R₂)SO₂R₄ wherein R₂ is hydrogen or alkyl having from one to four carbon atoms and R₄ is alkyl having from one to four carbon atoms, phenyl, pyridyl, benzyl or dialkoxyphenyl wherein said alkoxy has from one to four carbon atoms; —N(R₂)—CONR₅R₆ wherein R₂ is hydrogen or alkyl having from one to four carbon atoms, R₅ is alkyl having from one to four carbon atoms, benzyl or pyridyl and R₆ is hydrogen or alkyl having from one to four carbon atoms; —O—CONHR₇ wherein R₇ is alkyl having from one to four carbon atoms, phenyl, benzyl or pyridyl; hydroxy; alkanoyloxy having from one to four carbon atoms; alkoxy having from one to four carbon atoms; substituted alkyl wherein said alkyl has from one to five carbon atoms and said substituent is hydroxy, alkoxy having from one to four carbon atoms or —CONR₂R₆ wherein R₂ and R₆ are each hydrogen or alkyl having from one to four carbon atoms; and substituted alkoxy wherein said alkoxy has from two to four carbon atoms and said substituent is hydroxy or alkoxy having from one to four carbon atoms, with the proviso that other than the alpha-carbon atoms is substituted.

2. The method of claim 1 wherein Y is —$CH_2COR_1$ and $R_1$ is alkyl having from one to four carbon atoms.

3. The method of claim 2 wherein $R_1$ is methyl.

4. The method of claim 1 wherein Y is —$N(R_2)COR_3$ wherein $R_2$ is methyl and $R_3$ is alkyl having from one to four carbon atoms.

5. The method of claim 4 wherein $R_3$ is n-propyl.

6. The method of claim 1 wherein Y is —$N(R_2)SO_2R_4$ wherein $R_2$ is methyl.

7. The method of claim 6 wherein $R_4$ is methyl.

8. The method of claim 6 wherein $R_4$ is n-propyl.

9. The method of claim 6 wherein $R_4$ is benzyl.

10. The method of claim 6 wherein $R_4$ is 3-pyridyl.

11. The method of claim 1 wherein $R_4$ is phenyl.

12. The method of claim 1 wherein Y is —$N(R_2)CONR_5R_6$ wherein $R_2$ is methyl and $R_5$ and $R_6$ are each alkyl having from one to four carbon atoms.

13. The method of claim 12 wherein $R_5$ and $R_6$ are each methyl.

14. The method of claim 1 wherein Y is —O—$CONHR_7$ wherein $R_7$ is alkyl having from one to four carbon atoms.

15. The method of claim 14 wherein $R_7$ is ethyl.

16. The method of claim 1 wherein Y is said substituted alkyl.

17. The method of claim 16 wherein the alkyl of said substituted alkyl is ethylene and said substituent is isopropoxy.

18. The method of claim 16 wherein the alkyl of said substituted alkyl is ethylene and said substituent is —$CONR_2R_6$ wherein $R_2$ and $R_6$ are each methyl.

19. The method of claim 1 wherein Y is said substituted alkoxy.

20. The method of claim 19 wherein the alkoxy of said substituted alkoxy is 2-methylpropoxy and said substituent is 2-hydroxy.

* * * * *